United States Patent [19]
Müller et al.

[11] Patent Number: 4,678,482
[45] Date of Patent: Jul. 7, 1987

[54] PROCESS FOR PURIFYING HYDROGEN CHLORIDE GAS

[75] Inventors: Heinz Müller, Brühl; Elmar Lohmar, Cologne; Harald Scholz, Erftstadt, all of Fed. Rep. of Germany

[73] Assignee: Hoechst Aktiengesellschaft, Frankfurt am Main, Fed. Rep. of Germany

[21] Appl. No.: 885,013

[22] Filed: Jul. 14, 1986

[30] Foreign Application Priority Data

Jul. 26, 1986 [DE] Fed. Rep. of Germany ....... 3526801

[51] Int. Cl.$^4$ ............................................. B01D 53/14
[52] U.S. Cl. ........................................ 55/71; 423/488; 423/240
[58] Field of Search ................ 55/71; 423/240 R, 488

[56] References Cited

U.S. PATENT DOCUMENTS 4,003,723 1/1977 Schafer et al. .......................... 55/71

Primary Examiner—Charles Hart
Attorney, Agent, or Firm—Connolly and Hutz

[57] ABSTRACT

Hydrogen chloride gas obtained as a by-product in the production of chloroacetic acid by subjecting acetic acid to a catalytic chlorination reaction with chlorine gas in the presence of acetic anhydride and/or acetyl chloride is purified. The prepurified by-product still contains 0.1–3 vol % acetyl chloride and up to 0.1 vol % chloroacetyl chloride. For purification, the hydrogen chloride gas is passed through two zones series-connected together and scrubbed in countercurrent fashion. More particularly, it is scrubbed in the first zone with concentrated hydrochloric acid and in the second zone with concentrated sulfuric acid.

8 Claims, 1 Drawing Figure

U.S. Patent  Jul. 7, 1987  4,678,482
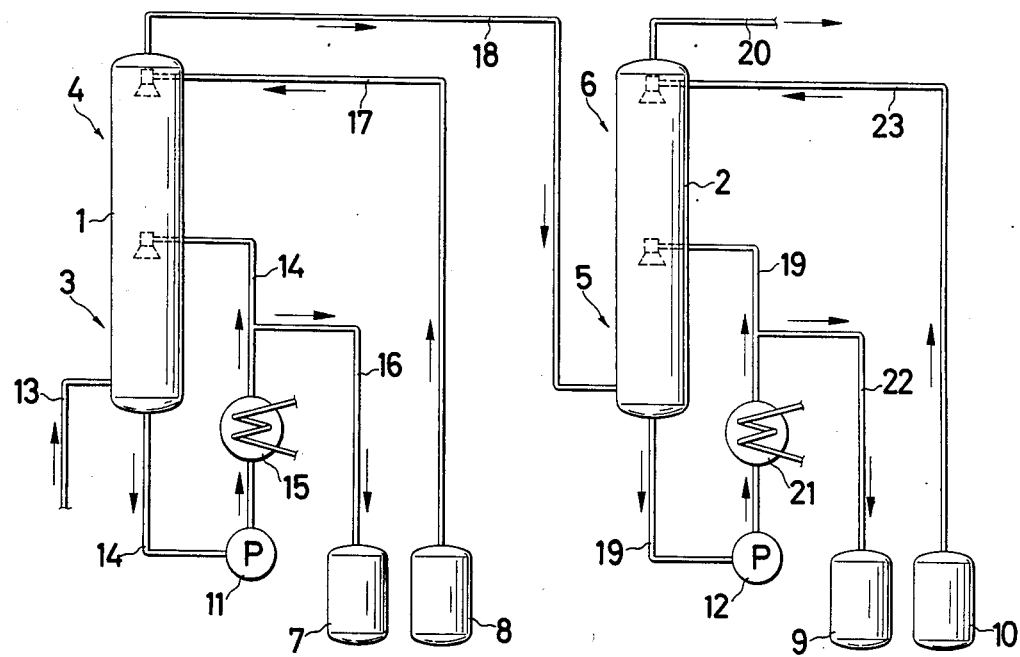

PROCESS FOR PURIFYING HYDROGEN CHLORIDE GAS

This invention relates to a process for purifying hydrogen chloride gas obtained in the continuous production of chloroacetic acid by subjecting acetic acid to a catalytic chlorination reaction with chlorine gas in the presence of acetic anhydride and/or acetyl chloride.

It has been described (cf. Ullmanns Enzyklopädie der technischen Chemie, 3rd edition, volume 5, pages 390 and 391) that chloroacetic acids can be made continuously by subjecting an at least 98% acetic acid to a chlorination reaction with chlorine with addition of acetic anhydride and/or acetyl chloride as a catalyst at a temperature of 85° C. or more. In order to utilize the hydrogen chloride obtained as a by-product in this process, it is necessary for condensable matter fractions contained therein, which are interesting accelerators, to be recycled into the acetic acid chlorination stage. To this end, the issuing gas is scrubbed countercurrently with fresh gas and or freed from the said condensable matter fractions by intense cooling.

A process of this kind for making chloroacetic acid has also been described in German Specification OS No. 19 19 476, wherein acetyl chloride and further off-gases, if any, coming from the reactor are recovered by cooling the gas issuing from the reactor to a temperature of at least 20° C. and additionally scrubbing it countercurrently with the mixture of acetic acid, acetic anhydride and/or acetyl chloride which is to undergo chlorination.

Hydrogen chloride purified in the manner just described still contains between 0.6 and 3 vol% carboxylic acid chlorides, predominantly in the form of acetyl chloride and some chloracetyl chloride, if any. Experience has shown such contaminated crude hydrogen chloride gas to be extremely corrosive, especially in those cases in which the gas is compressed for condensing condensable matter fractions contained in it. It has therefore been impossible heretofore to purify such crude hydrogen chloride gas in customary facilities to an extent making it possible for it to be used in chemical reactions. This is the reason why crude hydrogen chloride gas has just been adsorbed in water or hydrochloric acid, with formation of hydrochloric acid contaminated with acetic acid. In addition, it is a difficult and commercially unattractive procedure to separate the hydrochloric acid/acetic acid mixture distillatively, because of the low difference in the boiling points of acetic acid and the azeotropic hydrogen chloride/water-mixture. It has therefore often been necessary to discard hydrochloric acid contaminated with acetic acid.

German Specification DE-C No. 32 522 286 discloses a process for purifying hydrogen chloride gas obtained in the production o chloroacetic acid by subjecting acetic acid to chlorination, wherein the contaminated hydrogen chloride gas is scrubbed countercurrently with a liquid consisting substantially of about 20–80 wgt% $H_2SO_4$, about 15–60 wgt% acetic acid and about 5–50 wgt% water.

A disadvantage accompanying this process resides in the fact that circulated dilute sulfuric acid containing considerable proportions of acetic acid is obtained; in addition, the hydrochloric acid dissolved therein makes the sulfuric acid highly aggressive and difficult to handle. The acetic acid can be recovered only by very expensive purifying treatment.

It is therefore desirable to have a process permitting hydrogen chloride gas of the kind obtained in the production of chloroacetic acid by subjecting acetic acid to chlorination to be purified under commercially attractive conditions with recovery of materials which need not be subjected to expensive purifying treatment for reuse.

The present invention now provides a process for decontaminating prepurified hydrogen chloride gas in two countercurrent scrubbing zones series-connected together, the hydrogen chloride gas obtained as a by-product in the production of chloroacetic acid by subjecting acetic acid to a catalytic chlorination reaction with chlorine gas in the presence of acetic anhydride and/or acetyl chloride, and prepurified still containing about 0.1–3 vol% acetyl chloride and up to 0.1 vol % chloroacetyl chloride as contaminants, which comprises: scrubbing the hydrogen chloride gas in the first scrubbing zone with concentrated hydrochloric acid and in the second zone with concentrated sulfuric acid.

Each of the two scrubbing zones should conveniently be subdivided into a lower and upper portion.

In carrying out the present process, the hydrogen chloride gas to be purified should preferably be scrubbed initially in the lower portion of the first scrubbing zone at a temperature of 10°–50° C., advantageously 15°–25° C., with concentrated hydrochloric acid containing up to 15 wgt % acetic acid, preferably 7–10 wgt % acetic acid, and then in the upper portion of the first scrubbing zone at a temperature of 5°–40° C., preferably 18°–20° C., with concentrated hydrochloric acid.

It is also preferable for the lower portion of the first scrubbing zone to be supplied, per $m^3$ hydrogen chloride gas, measured at S.T.P., with 1–5 liter, advantageously 2–3 liter scrubbing liquid selected from concentrated hydrochloric acid and acetic acid, if any, and for the upper portion of the first scrubbing zone to be supplied, per $m^3$ hydrogen chloride gas, measured at S.T.P., with 0.05–1 liter, advantangeously 0.1 liter concentrated hydrochloric acid.

In carrying out the present process it is also preferable for the hydrogen chloride gas coming from the upper portion of the first scrubbing zone to be scrubbed initially in the lower portion of the second scrubbing zone at a temperature of 10°–40° C., advantageously 15°–20° C., with sulfuric acid containing up to 15 wgt %, advantageously 10 wgt %, water, and then in the upper portion of the second scrubbing zone at a temperature of 10°–30° C., preferably 18°–20° C., with concentrated sulfuric acid.

It is also preferable for the lower portion of the second scrubbing zone to be supplied, per $m^3$ hydrogen chloride gas, measured at S.T.P., with 2–10 liter, advantageously 5–6 liter, sulfuric acid containing up to 15 wgt %, advantageously up to 10 wgt % water, and for the upper portion of the second scrubbing zone to be supplied, per $m^3$ hydrogen chloride gas, measured at S.T.P., with 0.01–0.5 liter, advantageously 0.02–0.1 liter concentrated sulfuric acid.

The process of this invention permits hydrogen chloride gas of the kind obtained in the production of chloracetic acid by chlorination to be purified so that hydrogen chloride gas containing less than 10 ppm water and less than 5 ppm acetic acid is ultimately obtained.

The concentrated hydrochloric acid containing up to 15 wgt % acetic acid obtained in the first scrubbing zone can be recycled quantitatively into the monochloroacetic acid production stage and utilized for hydrolyzing acid chlorides or anhydrides.

The sulfuric acid obtained in the second scrubbing zone contains up to 15 wgt % water, less than 0.5 wgt % acetic acid and less than 0.1 wgt % hydrogen chloride. By blowing out with air, it is possible to obtain hydrogen chloride containing less than 10 ppm sulfuric acid which can directly be used for processing phosphate ore, for example.

The process of this invention will now be described with reference to the accompanying flwo scheme.

1800 m³/h (measured at S.T.P.) hydrogen chloride gas containing 0.15 vol % acetyl chloride, 0.01 vol % chloroacetylchloride and 0.1 vol % acetic acid as contaminants coming from a monochloroacetic acid production facility was introduced through line 13 into the first scrubbing zone 1. 4 m³/h (S.T.P.) scrubbing solution containing 39.8 wgt % hydrogen chloride and 8.9 wgt % acetic acid was circulated in the lower portion 3 of first scrubbing zone 1 through cycle line 14 by means of pump 11. Brine cooler 15 was used for maintaining the scrubbing solution at 17° C. The lower portion of the first scrubbing zone was column section 700 mm wide provided with 10 trays. Concentrated hydrochloric acid coming from reservoir 8 was introduced through line 17 into the upper portion 4 of the first scrubbing zone 1 at a rate of 180 l/h and at a temperature of 20° C. The upper portion of the first scrubbing zone was a column section 700 mm wide provided with 10 trays. Spent scrubbing solution was removed through line 16 and introduced into reservoir 7 (monochloracetic acid production).

The prepurified hydrogen chloride gas issueing from the first scrubbing zone through line 18 was introduced into the second scrubbing zone 2. In the lower portion 5 of the second scrubbing zone 2, the hydrogen chloride gas was scrubbed with 10 m³/h (S.T.P.) sulfuric acid containing 7.9 wgt % water, introduced through cycle line 19 by means of pump 12. The lower portion of the second scrubbing zone was a column section 700 mm wide provided with 10 trays.

By means of brine cooler 21, the liquid cycle 19 was maintained at 16° C. The upper portion 6 of the second scrubbing zone 2 was a column section 700 mm wide provided with 10 trays. It was supplied through line 23 with 60 l/h concentrated sulfuric acid coming from reservoir 10. The purified hydrogen chloride gas left the second scrubbing zone 2 through line 20. It was contaminated with less than 10 ppm water and less than 5 ppm acetic acid.

Spent sulfuric acid was introduced through line 22 into reservoir 9. It contained 7.9 wgt % water, less than 0.5 wgt % acetic acid and 0.09 wgt % hydrogen chloride.

We claim:

1. A process for decontaminating prepurified hydrogen chloride gas in two countercurrent scrubbing zones series-connected together, the hydrogen chloride gas obtained as a by-product in the production of chloroacetic acid by subjecting acetic acid to a catalytic chlorination reaction with chlorine gas in the presence of acetic anhydride and/or acetyl chloride, and prepurified still containing 0.1–3 vol % acetyl chloride and up to 0.1 vol % chloroacetyl chloride, which comprises: scrubbing the hydrogen chloride gas in the first scrubbing zone with concentrated hydrochloric acid and in the second scrubbing zone with concentrated sulfuric acid.

2. The process as claimed in claim 1, wherein the hydrogen chloride gas to be purified is scrubbed initially in the lower portion of the first scrubbing zone at a temperature of 10°–50° C. with concentrated hydrochloric acid containing up to 15 wgt % acetic acid and then in the upper portion of the first scrubbing zone at a temperature of 5°–40° C. with concentrated hydrochloric acid.

3. The process as claimed in claim 2, wherein the hydrogen chloride gas to be purified is scrubbed initially in the lower portion of the first scrubbing zone with concentrated hydrochloric acid containing 7–10 wgt % acetic acid.

4. The process as claimed in claim 2, wherein the lower portion of the first scrubbing zone is supplied, per m³ hydrogen chloride gas (measured at S.T.P.), with 1–5 liter scrubbing liquid selected from concentrated hydrochloric acid and acetic acid, if any.

5. The process as claimed in claim 2, wherein the upper portion of the first scrubbing zone is supplied, per m³ hydrogen chloride gas (measured at S.T.P.) with 0.05–1 liter concentrated hydrochloric acid.

6. The process as claimed in claim 2, wherein the hydrogen chloride gas coming from the upper portion of the first scrubbing zone is scrubbed initially in the lower portion of the second scrubbing zone at a temperature of 10°–40° C. with sulfuric acid containing up to 15 wgt % water, and then in the upper portion of the second scrubbing zone at a temperature of 10°–30° C. with concentrated sulfuric acid.

7. The process as claimed in claim 6, wherein the lower portion of the second scrubbing zone is supplied, per m³ hydrogen chloride gas (measured at S.T.P.) with 2–10 liter sulfuric acid containing up to 15 wgt % water.

8. The process as claimed in claim 6, wherein the upper portion of the second scrubbing zone is supplied, per m³ hydrogen chloride gas (measured at S.T.P.) with 0.01–0.5 liter concentrated sulfuric acid.

* * * * *